United States Patent [19]

Link et al.

[11] 4,297,636
[45] Oct. 27, 1981

[54] MAGNET AND PROBE MOUNTING MEANS ON A ROTATING HEAD OF MAGNETIC DEFECT TESTING APPARATUS

[75] Inventors: Hans Link, Reutlingen; Ulrich Dreher, Trochtelfingen, both of Fed. Rep. of Germany

[73] Assignee: Institut Dr. Friedrich Förster Prüfgerätebau, Reutlingen, Fed. Rep. of Germany

[21] Appl. No.: 62,708

[22] Filed: Aug. 1, 1979

[30] Foreign Application Priority Data

Sep. 2, 1978 [DE] Fed. Rep. of Germany ....... 2838388

[51] Int. Cl.³ ..................... G01R 33/00; G01N 27/82
[52] U.S. Cl. .................................... 324/262; 324/240
[58] Field of Search ............... 324/234, 236, 237–243, 324/260–262

[56] References Cited

U.S. PATENT DOCUMENTS

| | | | |
|---|---|---|---|
| 2,998,566 | 8/1961 | Cochran | 324/240 |
| 3,612,987 | 10/1971 | Placke et al. | 324/242 |
| 4,218,651 | 8/1980 | Ivy | 324/242 |

Primary Examiner—Gerard R. Strecker
Assistant Examiner—Walter E. Snow
Attorney, Agent, or Firm—George J. Netter

[57] ABSTRACT

The described rotating head effects A.C. field stray flux defect testing process using a rotating magnet yoke for high magnetizing field strength. The unit is compact and replaces a great number of conventional stationary devices in which the test article must be moved along a helical line past the magnet yoke. A speed of the rotating head of 900 revolutions per minute with an effective width of the probe support of 10 cm, achieves a testing speed of approximately 1.5 m/sec. This high testing speed makes the use of A.C. field stray flux testing at high magnetizing field strength possible from the economical point of view.

18 Claims, 7 Drawing Figures

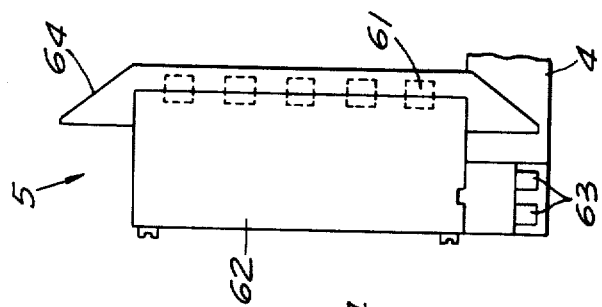
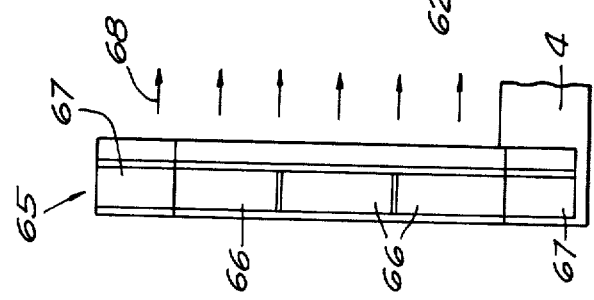
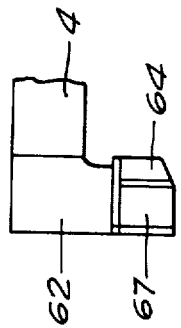
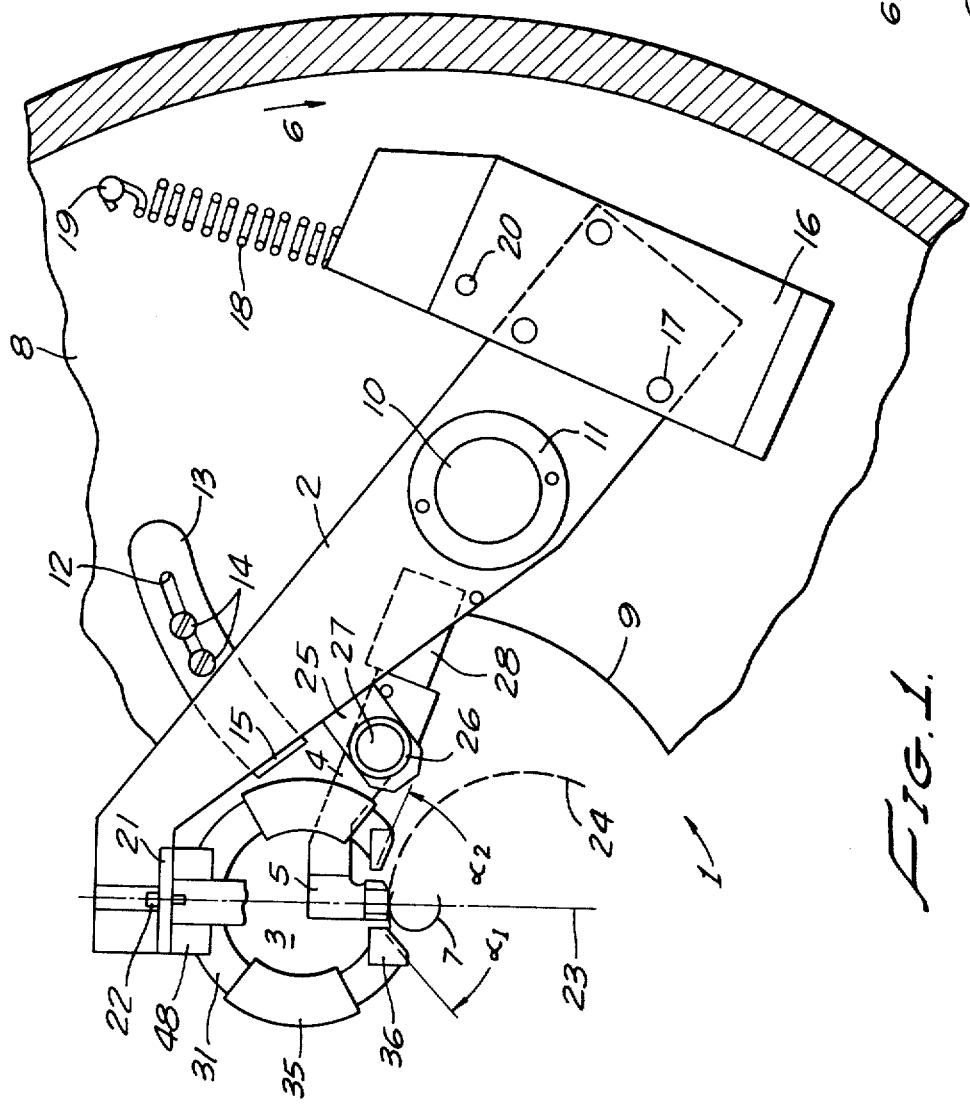

MAGNET AND PROBE MOUNTING MEANS ON A ROTATING HEAD OF MAGNETIC DEFECT TESTING APPARATUS

FIELD OF THE INVENTION

The present invention relates to a rotating head for magnetic testing of elongated ferromagnetic articles of circular cross-section for the existence of defects, including a rearwardly closed magnet yoke rotating about the article being tested and carrying an exciting winding suited for inducing high lend magnetic flux in the yoke, the poles of the yoke being directed towards the test article surface, and a probe support arranged between the poles and having at least one magnetic field-responsive test probe, the probe support being fastened to a probe lever mounted to swing in a plane perpendicular to the longitudinal axis of the test article and having a sliding shoe bearing resiliently against the test article surface.

THE PRIOR ART

A rotating magnetic head has been disclosed in West German published patent specification No. 1 946 142. The rotating head described in this publication includes a ring-shaped magnet yoke of mild steel with two inwardly directed projections carrying an existing winding, the test article being advanced in use between the tips of the projections, which take the form of a pole, in coaxial relation to the rotating ring-shaped magnet yoke. However, primary drawback of such a magnet yoke resides in the fact that it enables a great number of magnetic lines of forces to be closed between the poles or between the poles and the ring yoke, by-passing the test article. As a result thereof, obtaining sufficient magnetization is rendered more difficult and, on the other hand, the area between the poles intended for the test probes is "contaminated" by stray lines of flux. Also, such a magnet yoke cannot be used for alternating-current field magnetization since in this case magnetic hysteresis losses and eddy current losses because of the large quantities of iron employed would reach an absolutely excessive level. It would prove impossible to dissipate effectively the great amount of heat generated. Another disadvantage of a magnet yoke of this type is that different pole shoes would be required for each test article diameter so that an exchange of the pole shoes would become necessary with any change of the test article size in order to maintain the air gap constant at all times.

From West German published patent specification No. 20 25 807 a test device is known in which ferromagnetic material of circular cross-section is magnetized by means of a magnet yoke while being passed by the stationary magnet yoke along a helical path. During this motion, the surface of the material is scanned by a set of magnetic field-responsive diodes arranged in a block between the poles. The necessary high degree of magnetization can be achieved at higher frequencies.

As has been found out only quite recently, the use of a higher magnetizing energy in connection with a higher magnetizing frequency for stray flux testing methods results in a surprising increase of the ratio between useful signal and disturbance signal or so-called signal-to-noise ratio. Thus, a sufficiently high magnetizing field strength will even allow the use of the A.C. field stray flux measuring method for the solution of such testing problems which heretofore required a pre-magnetization in a longitudinal D.C. field in addition to the A.C. field magnetization in order to obtain the necessary signal-to-noise level. And this was, for instance, always the case when as a result of previous coldforming processes residual mechanical stresses were encountered in the test piece which, as is commonly known, result in a considerable increase of the noise level. However, premagnetization by D.C. fields in the longitudinal direction of the elongated test piece is in most cases undesirable because of the necessity to demagnetize the test pieces subsequently, a process which is always complicated and, in many cases, even impossible. Therefore, a testing device of the type described above, which can do without such premagnetization, would be highly advantageous. On the other hand, the limits within which helical movement of the test article can be produced, are very narrow. An article of considerable length, in particular, will render such a movement virtually impossible. Even in the case of an article of medium length, the speed in the circumferential direction maximally achievable will be too slow and thus lead to excessively long testing times. The published patent application mentioned above tries to eliminate this drawback by arranging several testing units in series. But, apart from the high costs involved, such arrangements result in excessive overall lengths of the testing units so that the latter cannot be accommodated in the areas intended for them.

OBJECT AND SUMMARY OF THE INVENTION

It is therefore an object of the present invention to provide a rotating magnetic test head which while offering an exceptionally favorable signal-to-noise ratio is easily adaptable to a large number of different test article diameters and provide, in addition, effective contact between the test probes and the test article surface.

By use of the described rotating head it is for the first time possible to carry out an A.C. field stray flux defect testing process using a rotating magnet yoke of high magnetizing field strength. The unit is compact and can replace a great number of conventional stationary devices in which the test article must be moved along a helical line past the magnet yoke. By way of example, a speed of the rotating head of 900 revolutions per minute with an effective width of the probe support of 10 cm, achieves a testing speed of approximately 1.5 m/sec. Moreover, this high testing speed makes the use of A.C. field stray flux testing at high magnetizing field strength possible from the economical point of view.

DESCRIPTION OF THE DRAWING

FIG. 1 shows a rotating head with magnet yoke and probe support.

FIGS. 5a–c depict a probe support.

DESCRIPTION OF A PREFERRED EMBODIMENT

Figure 3:
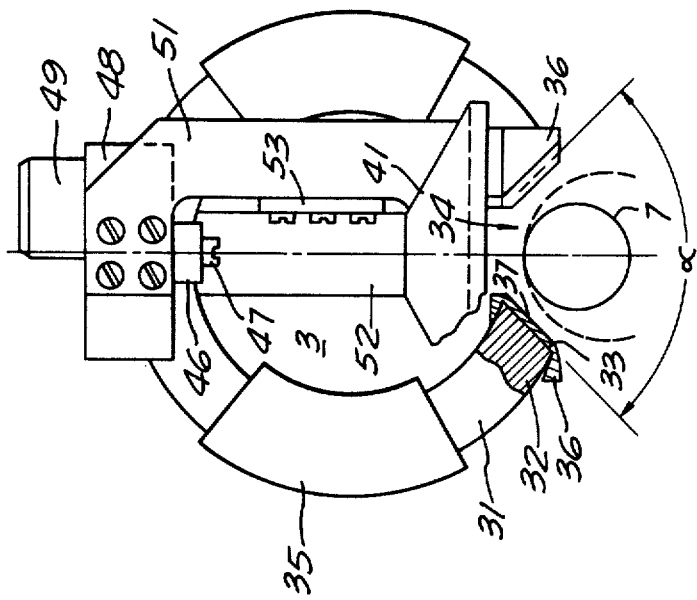
FIG. 3 is a side elevational view of the magnet yoke.

FIG. 1 is a cut-away view of a rotating head 1 constructed in accordance with the subject invention and including in its essential parts, a yoke lever 2 with a magnet yoke 3, a probe lever 4 with a probe support 5, and a counterweight 28 balancing the centrifugal force of the front portion of the probe lever 4 carrying the probe support 5. The travel of the probe lever 4 is limited by a stop not shown in the drawing. A spring—likewise not shown in the drawing—insures a uniform contact pressure between the probe support and the test article 7. The parts shown rotate in the direction indicated by arrow 6 about the test article 7 which is generally cylindrical and constructed of ferromagnetic material, the article 7 being driven by conveying means (not shown) in a longitudinal direction. A mounting plate 8 provided with a circular passage opening 9 for the test article 7 carries a shaft 10 about which the yoke lever 2 rotates in a bearing bushing. The frame which carries the mounting plate 8 and the drive means for rotating the mounting plate is likewise not shown. A knee-shaped stop plate 13 is provided with an elongated slot 12 and clamped to the mounting plate 8 by two screws 14 extending through the slot. The angularly projecting front portion 15 of the stop plate 13 acts as a stop for the leading side of the yoke lever 2 which can be adjusted as desired within the length of the slot 12. By suitable adjustment of the stop it can be insured that even in the presence of an article 7 of maximum diameter, curvature and eccentricity tolerances, it will still remain clear of the magnet yoke 3. In the event such tolerances should be exceeded, the yoke lever 2 can yield rearwardly, thus preventing damage to the magnet yoke 3.

The rear end of the yoke lever 2 has fixed to it by means of screws 17 a counterweight 16 to balance approximately the centrifugal force of the front portion of the lever carrying the magnet yoke 3. It has been found advantageous to make the counterweight 16 a little heavier than required for balancing so that with increasing rotational speeds, the contact pressure of the yoke lever 2 against the stop 15 will increase.

Normally, the yoke lever 2 is held in contact with the stop 15 by means of a spring 18 having one end fastened to the mounting plate 8 by means of a pin 19 and its other end fastened to the counterweight 16 by means of a pin 20. Mounted to the front portion of the yoke lever 2 at about the middle thereof is a bearing bracket 25, with a pin shaft carrying the probe lever 4 seated in its bearing bushing 26. The front tip of the yoke lever 2 carries a supporting plate 21 to which the magnet yoke 3 is fastened by means of screws 22.

Figure 2:
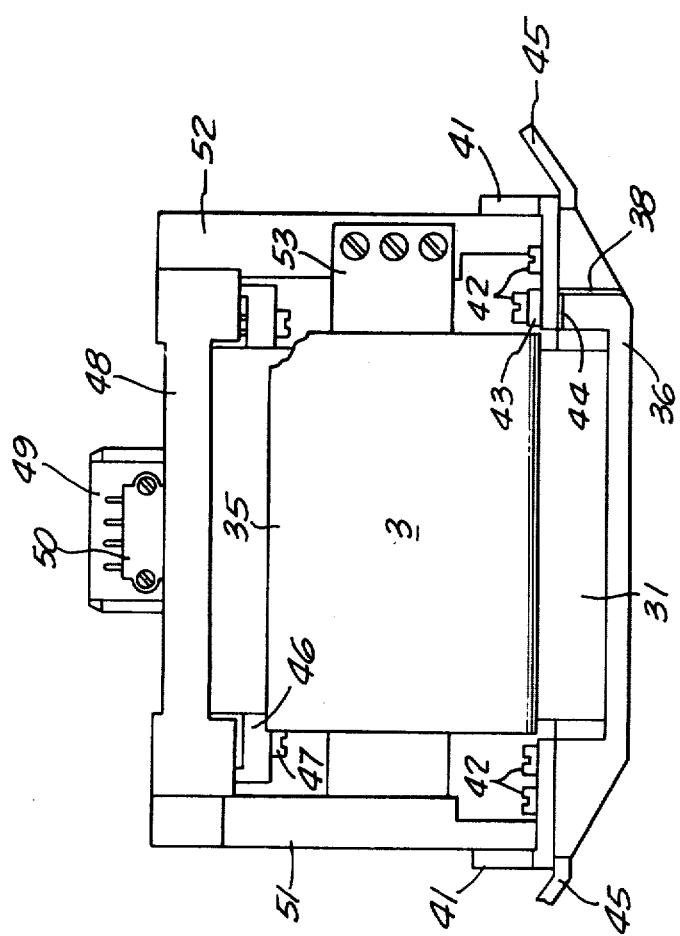
FIG. 2 is an end elevational view of the magnet yoke.

A more detailed and somewhat enlarged view of the magnet yoke 3 is given in FIGS. 2 and 3 to which reference is now made. The core 31 of the magnet yoke 3 is generally ring-shaped. A core of this type offers the magnetic properties required in the present case, namely, a high saturation induction and low watt losses per kilogram. Ring-shaped cores are obtained by winding a thin high-quality sheet metal band 32 upon a suitable form or mandrel. The desired cross-section is obtained by a suitable selection of the width of the sheet metal band 32 and the number of layers. For the purposes of this invention, the circular shape is particularly suitable because a considerable mechanical strength can be obtained thereby. After completion of the core sheet metal package, the package is dipped into a synthetic resin bath under vacuum conditions until all the gaps between the layers are completely filled. Thereafter, the synthetic resin is left to cure. The desired pole faces 33 of the ring core 31 are obtained by cutting out a small segment 34. The angle α of such segment depends upon the diameter range of the test articles 7 to be covered by the magnet yoke 3. FIG. 3 shows side by side the smallest (7) and the largest (24) diameters of the test articles that can be handled with a segment having the angle α as shown in the drawing. FIG. 1 shows at the left of the axis of symmetry 23 a test article 7 of the smallest possible range and the matching angle $\alpha_1$, and to the right of the axis of symmetry a test piece 24 of the largest possible range with the matching angle $\alpha_2$. It appears that only a small number of different magnet yokes 3 will be necessary to cover a large range of test piece dimensions. To this end, however, it is necessary that the segment 34 be kept as small as possible, i.e., not larger than is necessary to let the probe carrier 5 pass through.

Figure 4:
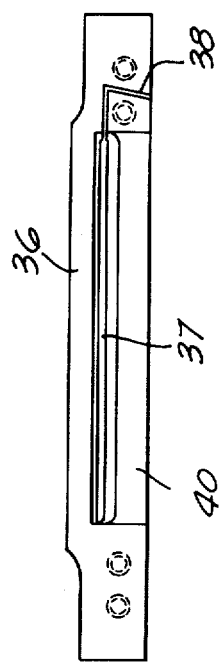
FIG. 4 shows a protective cap for the magnet yoke pole.

The sides of the ring core 31 carry a two-part winding 35 for exciting the magnetic flux. The winding 35 is given the necessary mechanical resistance to the centrifugal forces encountered by dipping it into synthetic resin. The pole faces 33 of the ring core 31 are protected by caps 36 (FIGS. 2-4). The protective caps 36 have the function to protect the poles 33 against contact with the test article 7 and to secure the strips 32 from coming apart under the influence of the centrifugal force. For this purpose, a rearwardly facing recess 40 provided in the protective caps encompasses the cross-section of the ring core 31 at the poles 33. In order to keep the effective air gap as small as possible, the material layer overlying the poles 33 must be as thin as possible. As a result, the necessary strength can be achieved only by the use of metallic materials. Without suitable protective measures, the penetrating A.C. field lines would build up high temperatures in the protective caps 36. Therefore, a material of low electric conductivity is employed, preferably a chrome-nickel steel. In addition, a slot 37 extends longitudinally through the full thickness of the material overlying the poles 33 terminating at one end in a gap 38 separating the material surrounding the slot and, thus, preventing the formation of short-circuit current. The slot 37 and gap 38 are filled with synthetic resin. The gap 38 extends along an oblique line to insure that the two dies of the slot will abut against each other when outwardly directed forces act upon the sides of the recess 40.

The two protective caps 36 are held together by an angle 41 to which they are fastened by screws 42, one of the screws passing through an insulating disk 43 and an insulating washer 44 to maintain the electric separation provided by the gap 38. At about its middle, the angle 41 has fastened to its bottom an additional contact plate 45 (omitted in FIG. 3) which causes the magnet yoke 3 to be lifted off when the test article exceeds its tolerance range.

The ring core 31 is suspended on a supporting rail 48 by means of clamping blocks 46 and screws 47, the supporting rail being in turn exchangeably connected to the supporting plate 21. The electric connection of the winding 35 is accomplished by a plug-and-socket connection 49 comprising a multiconductor connector 50. High mechanical strength is imparted to the magnet yoke 3 by cross-bracing between the supporting rail 48 and the angles 41. At the front, such cross-bracing takes the form of U-shaped bracket 51 to provide a passage for the probe support 5 during the exchange of the yoke. At the rear, the supporting rail 48 and the angle 41 are held together by means of a beam 52. A sheet metal strip 53 interconnecting the beam 52 and the bracket 51 improves the mechanical strength still further. The sheet metal strip 53 may also carry additional weights for balancing the different masses of the magnet yokes 3 for different test ranges so that no balancing of masses must be performed when the yokes are exchanged. The supporting rail 48, the bracket 51 and the beam 52 could form a short-circuited turn, either in connection with the metal strips 53, or else in connection with the protective caps 36. This is prevented by making either the beam 52 or the bracket 51 of a plastic material.

FIG. 5 is a separate, enlarged view of the probe support 5. Within the probe support, five field-responsive test probes 61 are equally spaced in the lengthwise direction of the test article. The probes 61 are accommodated in a center portion 62 mounted to the probe lever 4 by means of screws 63. Protection for the probes 61 is provided by a sliding shoe 64 having a sole-plate 65 of cemented carbide, the latter consisting of three separate plates 66 and two additional plates 67 forming sloping abutting surfaces. The special construction of the sole-plate 65 serves the following purpose: The test article has strong magnetic alternating flux flowing through a thin surface layer in the direction indicated by the arrows 68. When the sole-plate is in contact along a line with the surface, it coacts with the latter to form a short-circuited ring around the magnetic flux. At the points of contact, sparks may form and develop considerable disturbance signals. By making the sole-plate 65 of separate plates as shown, the disturbing voltage is reduced to a level that no sparks and, as a consequence, no disturbance signals will be produced.

Additional means are provided to avoid still another and similar possible source of disturbance. A short-circuit loop may form through the sole-plate 65, other parts of the probe support 5, and probe lever 4, the yoke lever 2, the guide of the test article (not shown) and the test article itself, which might also give rise to a disturbing spark formation. To prevent such disturbances, the center portion 62 of the probe support 5 is made of a non-conductive material.

If the magnetic field of the magnet yoke 3 were permitted to act for an extended period upon the test piece 7 not being advanced in the longitudinal direction, the latter would soon heat up to an unacceptable degree. Incidences of this type are prevented by means which automatically disconnect the magnet yoke 3 when the test piece comes to a standstill.

We claim:

1. A rotating head for magnetic defect testing of elongated cylindrical ferromagnetic test articles in which a rearwardly closed magnet yoke rotates about the test articles, a winding on said yoke excites magnetic flux therein, pole faces of the said magnet yoke are directed towards the test article surface, and a probe support is arranged between the pole faces including at least one field-responsive test probe, said probe support being fastened to a probe lever mounted to swing in a plane transversely perpendicular to the longitudinal axis of the test article and having a sliding shoe bearing resiliently against the test article surface, the improvement comprising:

a yoke lever mounted on the rotating head for swinging movement in a plane transversely perpendicular to the longitudinal axis of the test article, said yoke lever having one end interconnected with the magnet yoke and an end opposite said magnet yoke carrying a counterweight; and said probe lever being rotatively mounted on the yoke lever.

2. A rotating head as in claim 1, in which the counterweight substantially balances the weight of the magnet yoke.

3. A rotating head as in claim 1, in which the centrifugal force of the counterweight exceeds that of the magnet yoke.

4. A rotating head as in either of claims 1 or 2, in which the yoke lever bears resiliently against an adjustable stop.

5. A rotating head as in claim 1, in which the magnet yoke includes a ring-shaped core with two pole faces formed by cutting a segment out of the core.

6. A rotating head as in claim 5, in which the ring-shaped core includes a plurality of laminations bonded together by a synthetic resin.

7. A rotating head as in claim 5, in which a protective cap is provided in covering relationship over each pole face.

8. A rotating head as in claim 7, in which said protective caps are constructed of a high strength, low electrical conductivity metal.

9. A rotating head as in claim 8, in which that part of each protective cap lying immediately opposite the pole face has a thickness not greater than about 2 millimeters.

10. A rotating head as in either of claims 8 or 9, in which the protective caps are constructed of a chrome-nickel steel.

11. A rotating head as in claim 7, in which each protective cap includes a first portion directly opposite the pole face and other portions outwardly of said first portion, said cap first portion including a slot within the cap material extending across the entire pole face and into a gap in said other portions, and the slot and gap being filled with an electrically nonconductive material.

12. A rotating head as in claim 11, in which the gap extends obliquely with respect to the pole face such that the walls defining the gap bear against each other when outwardly directed forces are exerted upon the inner surfaces of the protective cap by the core.

13. A rotating head as in either of claims 7 or 8, in which the protective caps are mechanically interconnected by an angle.

14. A rotating head as in either of claims 7 or 8, in which the protective caps are mechanically interconnected by a supporting rail also carrying the magnet yoke.

15. A rotating head as in claim 14, in which means providing mechanical connection between the protective caps and supporting rail is constructed of an electrically nonconductive material.

16. A rotating head as in claim 1, in which the probe lever has a pivot axis located outside the magnet yoke.

17. A rotating head as in claim 1, in which the sliding shoe has a sole-plate constructed of cemented carbide.

18. A rotating head as in claim 17, in which the sliding shoe is constructed of a plurality of plates extending longitudinally of the test piece.

* * * * *